United States Patent [19] [11] 4,304,909
Saikawa et al. [45] Dec. 8, 1981

[54] PROCESS FOR PRODUCING 7-(D(—)-α-(4-ETHYL-2,3-DIOXO-1-PIPERAZINECARBOXAMIDO)-α-(4-HYDROXYPHENYL)ACETAMIDO)-3-(5-(1-METHYL-1,2,3,4-TETRAZOLYL)THIOMETHYL)-Δ³-CEPHEM-4-CARBOXYLIC ACID AND A PHARMACEUTICALLY ACCEPTABLE SALT THEREOF

[75] Inventors: Isamu Saikawa; Shuntaro Takano; Kaishu Momonoi; Isamu Takakura, all of Toyama; Chiaki Kutani, Funabashi; Kiyoshi Tanaka, Oshimamachi; Kenshin Hayashi, Tonami, all of Japan

[73] Assignee: Toyama Chemical Co., Ltd., Tokyo, Japan

[21] Appl. No.: 69,545

[22] Filed: Aug. 24, 1979

Related U.S. Application Data

[62] Division of Ser. No. 945,346, Sep. 25, 1978, Pat. No. 4,237,280.

[30] Foreign Application Priority Data

Sep. 27, 1977 [JP] Japan .................................. 52/115126
Sep. 27, 1977 [JP] Japan .................................. 52/115127

[51] Int. Cl.³ .......................................... C07D 501/37
[52] U.S. Cl. ...................................... 544/027; 424/246; 544/026

[58] Field of Search ................... 424/270, 246; 544/27, 544/21, 26

[56] References Cited

U.S. PATENT DOCUMENTS

| | | | |
|---|---|---|---|
| 3,641,021 | 2/1972 | Ryan | 544/27 |
| 3,781,282 | 12/1973 | Garbrect | 260/243 C |
| 3,954,745 | 5/1976 | Jackson et al. | 260/243 C |
| 4,064,345 | 12/1977 | Kaplan | 544/27 |
| 4,100,008 | 7/1978 | Toshiyara | 544/20 |
| 4,103,008 | 7/1978 | Toshiyara et al. | 544/27 |
| 4,112,090 | 9/1978 | Saikawa et al. | 424/291 |
| 4,117,126 | 9/1978 | Yamara et al. | 544/27 |
| 4,145,418 | 3/1979 | Kuwara et al. | 544/27 |

FOREIGN PATENT DOCUMENTS 53-10075 4/1978 Japan .

Primary Examiner—Nicholas S. Rizzo
Attorney, Agent, or Firm—Oblon, Fisher, Spivak, McClelland & Maier

[57] ABSTRACT

The N,N-dimethylacetamide adduct of 7-[D(—)-α-(4-ethyl-2,3-dioxo-1-piperazinecarboxamido)-α-(4-hydroxyphenyl)acetamido]-3-[5-(1-methyl-1,2,3,4-tetrazolyl)-thiomethyl]-Δ³-cephem-4-carboxylic acid, a process for the production thereof, and a process for producing said acid and a pharmaceutically acceptable salt thereof through said adduct.

12 Claims, No Drawings

PROCESS FOR PRODUCING 7-(D(−)-α-(4-ETHYL-2,3-DIOXO-1-PIPERAZINECARBOXAMIDO)-α-(4-HYDROXYPHENYL)ACETAMIDO)-3-(5-(1-METHYL-1,2,3,4-TETRAZOLYL)THIOMETHYL)-Δ³-CEPHEM-4-CARBOXYLIC ACID AND A PHARMACEUTICALLY ACCEPTABLE SALT THEREOF

This is a division, of application Ser. No. 945,346, filed Sept. 25, 1978; now U.S. Pat. No. 4,237,280.

This invention relates to the N,N-dimethylacetamide adduct of 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid represented by the formula (I),

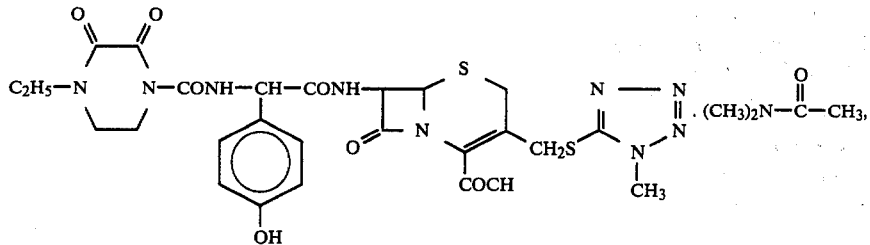

a process for the production thereof, and relates further to a process for producing 7-[D(−)-α-(4-ethyl-2,3-dioxo-1-piperazinecarboxamido)-α-(4-hydroxyphenyl)-acetamido]-3-[5-(1-methyl-1,2,3,4-tetrazolyl)thiomethyl]-Δ³-cephem-4-carboxylic acid represented by the formula (II),

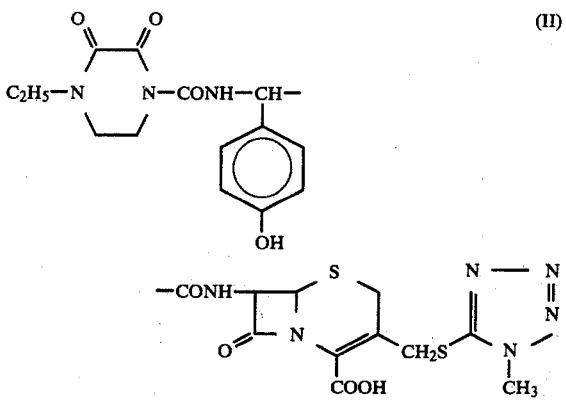

and a pharmaceutically acceptable salt thereof without having the N,N-dimethylacetamide in said compound represented by the formula (I).

The compound represented by the formula (II) or a pharmaceutically acceptable salt thereof is now in developmental stage as a therapeutic agent, because, as disclosed in Japanese Patent Publication No. 10,075/78, the compound and the salt are excellent in antibacterial activity against not only gram-positive but also gram-negative bacteria, and low in toxicity, and have a broad antibacterial spectrum.

According to Japanese Patent Publication 10,075/78, the compound represented by the formula (II) is obtained by the condensation of D(−)-α-(4-ethyl-2,3-dioxo-1-piperazinecarboxamido)-α-(4-hydroxyphenyl)acetic acid or a reactive derivative thereof such as, for example, an acid chloride or a mixed acid anhydride, with 7-amino-3-[5-(1-methyl-1,2,3,4-tetrazolyl)thiomethyl]-Δ³-cephem-4-carboxylic acid in the presence of an inert solvent, such as methylene chloride or the like. Such a reaction is generally known as acylation of 7-aminocephalosporins and is frequently employed.

According to Japanese Patent Publication No. 10,075/78 the acylation is carried out in the presence of one or more solvents inert to the reaction such as, for example, water, acetone, tetrahydrofuran, dioxane, acetonitrile, dimethylformamide, methanol, ethanol, methoxyethanol, diethyl ether, di-isopropyl ether, benzene, toluene, methylene chloride, chloroform, ethyl acetate, and methyl isobutyl ketone. In such a process, however, isolation of the intended product from the reaction mixture requires extraction with a solvent, which complicates the procedure, and difficulty is encountered in separating the product from by-products.

Therefore, no advantageous commercial production of the compound represented by the formula (II) or a pharmaceutically acceptable salt thereof is expectable.

The use of N,N-dimethylformamide and N,N-dimethyl acetamide as solvents in acylation is disclosed in U.S. Pat. No. 3,502,665 and the use of N,N-dimethylacetamide is disclosed in Japanese Patent Application Kokai (Laid-Open) No. 48,688/76. However, in the experiment of the present inventors, even if N,N-dimethylformamide is used in the reaction in this invention, there is observed neither precipitation of the compound of the formula (I) from the reaction mixture nor formation of highly pure cephalosporin of the formula (II) on simple treatment of the reaction mixture as produced with a solvent.

The present inventors have, therefore, made extensive research to achieve an uncomplicated process for producing the compound represented by the formula (II) and a pharmaceutically acceptable salt thereof in high purity and high yield. As a result, it has unexpectedly been found that when the acylation is carried out in the presence of N,N-dimethylacetamide, the reaction smoothly proceeds and the compound represented by the formula (I) crystallizes out in high purity and high yield and that when the resulting compound of the formula (I) is treated with a solvent, the N,N-dimethylacetamide is easily split off, yielding the compound of the formula (II) in high purity and high yield with sufficient easiness for the commercial production. On further study, it has been found that when the compound of the formula (II) containing by-products obtained by the conventional method is treated with N,N-dimethylacetamide, the compound of the formula (I) is formed in the form of highly pure crystals and that the compound of the formula (II) is produced as pure product by subsequently effecting the above-mentioned treatment. It has also been discovered that the compound per se of the formula (I) has an excellent antibacterial activity.

An object of this invention is to provide a novel intermediate of the formula (I) which is useful in the production of useful compounds represented by the formula (II).

Another object of this invention is to provide the compound of the formula (I) which is useful as an antibacterial activity.

A further object of this invention is to provide a process for producing the compound of the formula (I).

A still further object of this invention is to provide another process for producing the compound of the formula (I).

A still further object of this invention is to provide a process for producing the compound of the formula (II) and its pharmaceutically acceptable salt by treating the compound of the formula (I) with a solvent to remove N,N-dimethylacetamide.

A further object of this invention is to provide a process for commercially advantageously producing the compound of the formula (II) and its pharmaceutically acceptable salt through the method (a), which is described in detail hereinafter.

Other objects and advantages of this invention will become apparent from the following description.

According to this invention, the compound of the formula (I) can be obtained by either (a) reacting 7-amino-3-[5-(1-methyl-1,2,3,4-tetrazolyl)thiomethyl]-$\Delta^3$-cephem-4-carboxylic acid hydrochloride represented by the formula (III),

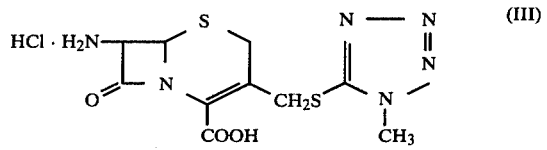

with a reactive derivative of D(−)-α-(4-ethyl-2,3-dioxo-1-piperazinecarboxamido)-α-(4-hydroxyphenyl)acetic acid represented by the formula (IV),

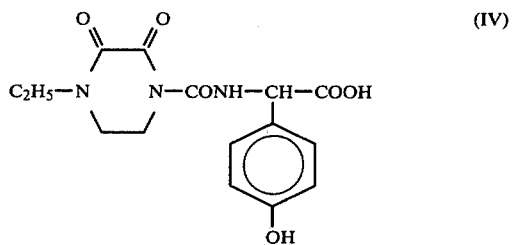

in the presence of N,N-dimethylacetamide as the solvent (method (a)), or (b) treating the compound of the formula (II) obtained by a known method with N,N-dimethylacetamide (method (b)).

Further, according to this invention, the compound of the formula (II) is produced by treating with a solvent the compound of the formula (I), obtained by the method (a) or (b), to remove the N,N-dimethylacetamide.

In particular, in the novel process for producing the compound of the formula (II) or its pharmaceutically acceptable salt through the method (a), the compound represented by the formula (II) and its pharmaceutically acceptable salt are commercially simply obtained as pure product in a high yield, and in the process through the method (b), the compound represented by the formula (II) and its pharmaceutically acceptable salt are very easily purified.

The reactive derivative of D(−)-α-(4-ethyl-2,3-dioxo-1-piperazinecarboxamido)-α-(4-hydroxyphenyl)acetic acid of the formula (IV) to be used as acylating agent in the method (a) of this invention may be previously prepared from the corresponding acid in N,N-dimethylacetamide as solvent and the reaction mixture as thus produced may subsequently be used in the acylation reaction or the reactive derivative may previously be prepared in a solvent other than N,N-dimethylacetamide and then used as prepared, or may be isolated and purified before use. In preparing the reactive derivative, it is also possible to use, in addition to N,N-dimethylacetamide, a suitable auxiliary solvent such as, for example, acetonitrile, acetone, methylene chloride or chloroform. The residual auxiliary solvent in the reaction system is not objectionable to the acylation in this invention.

The reactive derivatives of D(−)-α-(4-ethyl-2,3-dioxo-1-piperazinecarboxamido)-α-(4-hydroxyphenyl)acetic acid of the formula (IV) include acid halides and reaction products of the compound of the formula (IV) with a Vilsmeier reagent. These reactive derivatives are prepared by a conventional method. The halogenating agent used in the production of said acid halide or the Vilsmeier reagent include, for example, phosgene, thionyl chloride, phosphorus trichloride, phosphorus tribromide, phosphorus oxychloride, phosphorus oxybromide, phosphorus pentachloride, trichloromethyl chloroformate, and oxalyl chloride. A preferred reactive derivative of the compound of the formula (IV) is the reaction product of the compound (IV) with a Vilsmeier reagent.

Acylation of 7-amino-3-[5-(1-methyl-1,2,3,4-tetrazolyl)thiomethyl]-$\Delta^3$-carboxylic acid hydrochloride of the formula (III) is effected by use of the above-noted reactive derivative of the compound of the formula (IV). Although it is sufficient to use equimolar quantities of the compound of the formula (IV) and the compound of the formula (III) in the acylation reaction, a recommendable practice is to use a slight excess of the reactive derivative of the compound of the formula (IV) in order to allow the not easily available compound of the formula (III) to react efficiently.

The acylation is carried out at a temperature generally from about −40° to about 30° C., preferably from about −30° to about 0° C. and the reaction is completed in about 15 minutes to about 2 hours. Since it is desirable to keep the reaction system anhydrous, the reagents and the solvents are thoroughly dried before use and the reaction is carried out under a nitrogen atmosphere. A dehydrating agent such as trimethylchlorosilane can be added to remove the moisture which may be present in the reaction system.

After the above acylation, a base such as sodium hydrogen carbonate or the like and water are added to the reaction mixture, and the mixture is stirred, upon which the N,N-dimethylacetamide adduct of the formula (I) substantially free from by-products precipitates as crystals. Accordingly, these crystals are collected by filtration to obtain the N,N-dimethylacetamide adduct of the formula (I) of this invention easily. The amount of water added at the end of the acylation is 0.25 to 2.5 times, preferably 1.0 to 1.5 times, that of the N,N-dimethylacetamide used in the reaction. Since it is desirable that at this time the pH of the reaction mixture is 1 to 3, the pH is appropriately adjusted by adding a base such as sodium hydrogen carbonate or the like.

The method (b) is carried out in the following way: The compound of the formula (II) containing by-products, which is obtained by a known method such as that described in Japanese Patent Publication No. 10,075/78 is added to N,N-dimethylacetamide to form the compound of the formula (I), which is then admixed with water and treated as described above in connection with the method (a), yielding the highly pure compound of the formula (I).

In this invention, the compound of the formula (II) may be in the form of a hydrate, regardless of whether it is the starting material or the objective compound.

The pure compound of the formula (II) is obtained by stirring the suspension of N,N-dimethylacetamide adduct of 7-[D(—)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid represented by the formula (I), obtained by the aforementioned method (a) or (b), in water, a hydrophilic organic solvent such as methanol, ethanol, acetonitrile or the like or a hydrophobic organic solvent such as methylene chloride, benzene or the like, or a mixed solvent of the hydrophilic or hydrophobic organic solvent and water; or, alternatively, by first dissolving the adduct in water, said hydrophilic or hydrophobic organic solvent or said mixed solvent in the presence or absence of base and precipitating crystals from the solution by, for example, neutralyzation or dilution with water. The above treatment with water or a mixture of water and the hydrophilic solvent is preferred.

The compound of the formula (II) can be converted into a pharmaceutically acceptable salt in a conventional manner. Such salts include those with alkali metals such as sodium, potassium and the like, alkaline earth metals such as calcium, magnesium and the like, with ammonium, and with pharmaceutically acceptable nitrogen-containing organic bases. Typical examples of such bases include procain, dibenzylamine, N-benzyl-β-phenethylamine, 1-ephenamine and N,N'-dibenzylethylenediamine.

The invention is illustrated below in detail with reference to Examples, but the invention is not limited thereto.

EXAMPLE 1

(1) In 16 ml of N,N-dimethylacetamide was dissolved 4.0 g of D(—)-α-(4-ethyl-2,3-dioxo-1-piperazinecarboxamido)-α-(4-hydroxyphenyl)acetic acid. To the solution, while being cooled at −20° to −22° C., was added 2.02 g of phosphorus oxychloride over a period of 10 minutes and the mixture was allowed to react for 1 hour at this temperature. A mixture of 4.0 g of 7-amino-3-[5-(1-methyl-1,2,3,4-tetrazolyl)thiomethyl]-Δ³-cephem-4-carboxylic acid hydrochloride, 12 ml of N,N-dimethylacetamide and 0.60 g of trimethylchlorosilane was added dropwise to the above reaction mixture over a period of 7 minutes, while keeping it at −20° to −22° C. The resulting mixture was allowed to react for 90 minutes at the same temperature. The reaction mixture was then brought to room temperature, to which 3.5 g of sodium hydrogen carbonate and 28.8 ml of water were added and the mixture was stirred for 2 hours to precipitate crystals. To the mixture was added 1.4 ml of water to dilute the mixture and the mixture was stirred for 2 hours at room temperature and for one hour with ice-cooling. The crystals thus precipitated was collected by filtration, washed with 8 ml of aqueous N,N-dimethylacetamide (containing 80% by volume of water), and dried to obtain 6.85 g of the N,N-dimethylacetamide adduct of 7-[D(—)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid, m.p. 161°–163° C. (decomp.), yield 85.3%.

IR(KBr) cm⁻¹: νC=O 1773, 1702, 1670 NMR (D₂O-NaHCO₃) ppm values; 1.20 (3H, t, —CH₂CH₃), 2.11

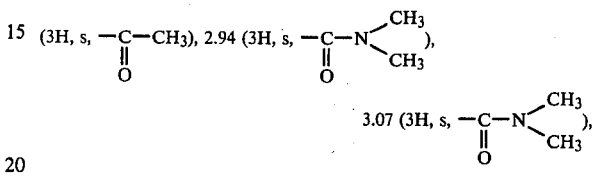

3.20–4.20 (10H, m, >CH₂×5), 3.97 (3H, s, >N—CH₃), 4.94 (1H, d, C₆—H), 5.46 (1H, s, Cα—H), 5.66 (1H, d, C₇—H), 7.09 (4H, ABq, >C₆H₄)

(2) To a mixture of 12.5 ml of acetonitrile and 6.2 ml of water was added 5.5 g of the N,N-dimethylacetamide adduct of 7-[D(—)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid. To the mixture was added 0.50 g of sodium hydrogen carbonate to dissolve the adduct. The resulting solution was heated to 35° C., and 1.0 ml of 6 N hydrochloric acid was added, after which the solution was stirred for 1 hour at the same temperature, upon which white crystals precipitated. To the mixture while being maintained at 35° C., was added 14.8 ml of water. The resulting mixture was cooled gradually to room temperature. The precipitated crystals were collected by filtration and dried to obtain 4.6 g of 7-[D(—)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid hydrate.

The objective compound obtained by the above procedure contained substantially no by-products such as 7-[D(—)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ²-cephem-4-carboxylic acid and a γ-lactonized product of the compound of the formula (II) and could easily be isolated in the form of pure white crystals. For instance, the absorbance at 400 nm of the objective compound measured using water as control was very small.

EXAMPLE 2

(1) In a mixture of 8 ml of N,N-dimethylacetamide and 1 ml of acetonitrile was dissolved 2.0 g of D(—)-α-(4-ethyl-2,3-dioxo-1-piperazinecarboxamido)-α-(4-hydroxyphenyl)acetic acid. To the resulting solution was added dropwise a mixture of 0.65 g of trichloromethyl chloroformate and 1 ml of acetonitrile over a period of 15 minutes at −20° C. After the dropwise addition, the mixture was allowed to react at −20° C. for 1 hour. To the reaction mixture was added dropwise a mixture of 2.0 g of 7-amino-3-[5-(1-methyl-1,2,3,4-tetrazolyl)thiomethyl]-Δ³-cephem-4-carboxylic acid hydrochloride, 6 ml of N,N-dimethylacetamide and 0.3 g of trimethyl chlorosilane over a period of 10 minutes at −20° C. The resulting mixture was allowed to react at −20° C. for 90 minutes. The reaction mixture was concentrated under reduced pressure for 30 minutes (bath temperature 30° C.; 15 mmHg) to remove the acetonitrile. To the residue were added 1.2 g of sodium hydrogen carbonate and 14 ml of water and the resulting solution was stirred for 2 hours at room temperature to precipitate crystals. The mixture was again diluted with 7 ml of water and stirred for 2 hours at room temperature and then for 1 hour with ice-cooling. The precipitated crystals were collected by filtration, washed with 4 ml of aqueous N,N-dimethylacetamide (containing 80% by volume of water), and dried to obtain 3.50 g of the N,N-dimethylacetamide adduct of 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)-thiomethyl]-Δ³-cephem-4-carboxylic acid, yield 87.1%. The melting point and the IR and NMR values were in agreement with those obtained in Example 1-(1).

(2) Using the adduct obtained above, the reaction in Example 1-(2) was repeated to obtain 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)-thiomethyl]-Δ³-cephem-4-carboxylic acid hydrate.

EXAMPLE 3

(1) To a suspension of 2.0 g of D(−)-α-(4-ethyl-2,3-dioxo-1-piperazinecarboxamido)-α-(4-hydroxyphenyl)acetic acid in 20 ml of methylene chloride was added 1.52 ml of trimethylchlorosilane. To the mixture was added dropwise with cooling 1.58 ml of triethylamine over a period of 3 minutes at 10° to 15° C., and the reaction was allowed to proceed at the same temperature for 1 hour. The reaction mixture was cooled to −25° C., and 0.46 ml of N,N-dimethylformamide and 1.66 g of oxalyl chloride were added in this order, after which the reaction was allowed to proceed for 1 hour at −20° to −25° C. The reaction mixture was freed from the solvent by distillation under reduced pressure. The residue was dissolved in 8 ml of N,N-dimethylacetamide and the resulting solution was added dropwise to a previously cooled solution of 2.0 g of 7-amino-3-[5-(1-methyl-1,2,3,4-tetrazolyl)thiomethyl]-Δ³-cephem-4-carboxylic acid hydrochloride in 6 ml of N,N-dimethylacetamide over a period of 4 minutes at −20° to −22° C. The reaction was allowed to proceed at −20° to −22° C. for 90 minutes. The reaction mixture was brought to room temperature, and diluted with 14 ml of water, after which the pH of the diluted mixture was adjusted to 2 with sodium hydrogen carbonate. The mixture was stirred for 2 hours to precipitate crystals. To the mixture was again added 7 ml of water, and the mixture was stirred for 2 hours at room temperature and then for 1 hour with ice-cooling. The precipitated crystals were collected by filtration, washed with 4 ml of aqueous N,N-dimethylacetamide (containing 80% by volume of water) and dried to obtain 3.25 g of the N,N-dimethylacetamide adduct of 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid, yield 80.8%. The melting point and the IR and NMR values were in agreement with those of the corresponding compound obtained in Example 1.

(2) To 20 ml of aqueous methanol (containing 80% by volume of water) was added 2.0 g of the N,N-dimethylacetamide adduct of 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid. The mixture was stirred for 1 hour at room temperature, and then for 1 hour with ice-cooling. The crystals were collected by filtration and dried to obtain 1.72 g of 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)-thiomethyl]-Δ³-cephem-4-carboxylic acid hydrate, yield 95.0%.

EXAMPLE 4

(1) A solution was prepared by slowly adding 2.91 g of 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid hydrate obtained by following the procedure described in the Example of Japanese Patent Application Kokai (Laid-Open) 70,788/76 to 12 ml of N,N-dimethylacetamide. To the solution, while maintaining the solution at 40° to 45° C., was added dropwise 18 ml of water. The mixture was cooled to room temperature and stirred for 12 hours at this temperature, and then stirred for 1 hour with cooling. The precipitated crystals were collected by filtration, washed with 3.0 ml of cooled aqueous N,N-dimethylacetamide (containing 80% by volume of water), and dried to obtain 3.03 g of the N,N-dimethylacetamide adduct of 7-[D(−)-α-(4-ethyl-2,3-dioxo-1-piperazinecarboxamido)-α-(4-hydroxyphenyl)acetamido]-3-]5-(1-methyl-1,2,3,4-tetrazolyl)-thiomethyl]-Δ³-cephem-4-carboxylic acid, yield 94.4%. The melting point and the IR and NMR values were in agreement with those of the corresponding compound obtained in Example 1-(1).

(2) Using the adduct obtained above, the reaction of Example 1-(2) was repeated to obtain 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)-thiomethyl]-Δ³-cephem-4-carboxylic acid hydrate.

What is claimed is:

1. A process for producing the N,N-dimethylacetamide adduct of 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid represented by the formula (I),

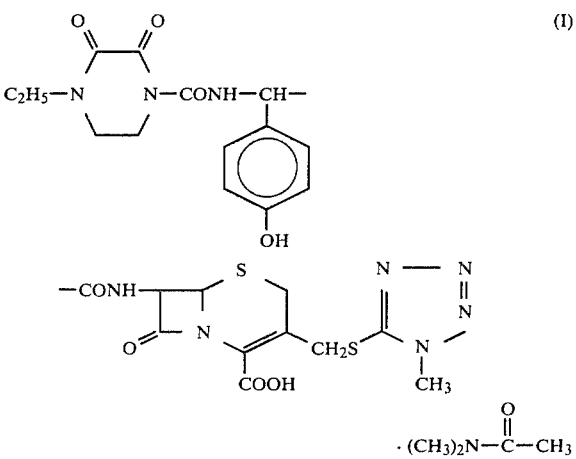

which comprises acylating the cephem compound represented by the formula (III),

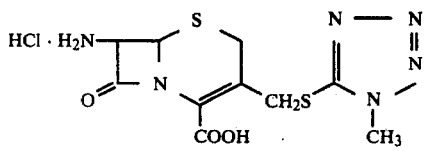

at the 7-amino group of said cephem compound (III), with a reactive derivative of the compound represented by the formula (IV),

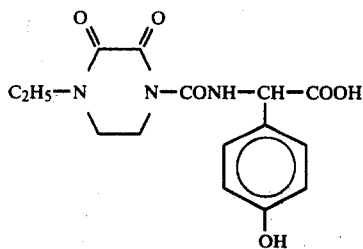

under anhydrous conditions in the presence of N,N-dimethylacetamide as the solvent for the said compounds (III) and (IV) to produce a solution of the acylated product and recovering the said adduct (I) as a precipitate from the solution.

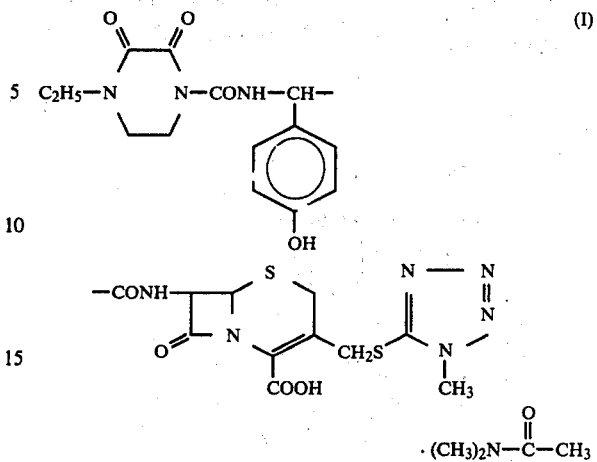

with a solvent for N,N-dimethylacetamide to remove the N,N-dimethylacetamide and to liberate compound (II).

3. A process for producing 7-[D(—)-α-(4-ethyl-2,3-dioxo-1-piperazinecarboxamido)-α-(4-hydroxyphenyl)-acetamido]-3-[5-(1-methyl-1,2,3,4-tetrazolyl)thiomethyl]-Δ³-cephem-4-carboxylic acid represented by the formula (II),

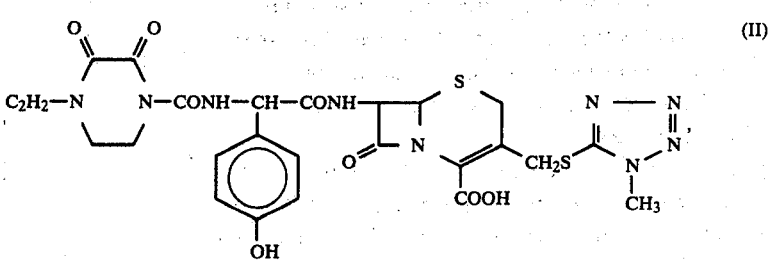

2. A process for producing 7[D(—)-α-(4-ethyl-2,3-dioxo-1-piperazinecarboxamido)-α-(4-hydroxyphenyl)-acetamido]-3-[5-(1-methyl-1,2,3,4-tetrazolyl)thiomethyl]-Δ³-cephem-4-carboxylic acid represented by the formula (II),

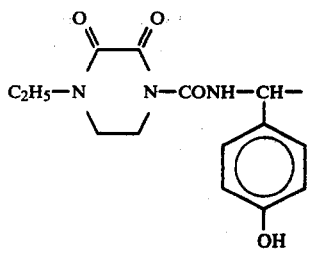

which comprises acylating the cephem compound represented by the formula (III),

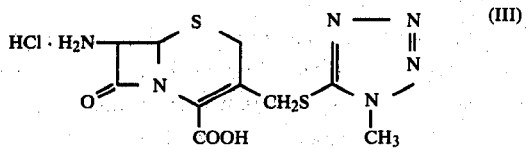

at the 7-amino group of said cephem compound (III), with a reactive derivative of the compound represented by the formula (IV),

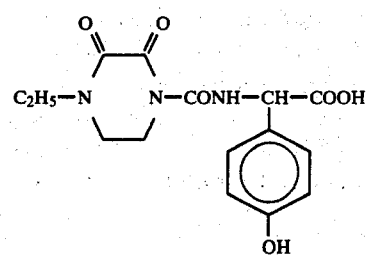

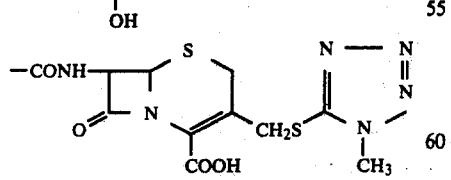

which comprises treating the N,N-dimethylacetamide adduct of 7-[D(—)-α-(4-ethyl-2,3-dioxo-1-piperazinecarboxamido)-α-(4-hydroxyphenyl-)acetamido]-3-[5-(1-methyl-1,2,3,4-tetrazolyl)thiomethyl]-Δ³-cephem-4-carboxylic acid represented by the formula (I), under anhydrous conditions in the presence of N,N-dimethylacetamide as the solvent for the said compounds (III) and (IV) to produce a solution of the acylated product, recovering as a precipitate the resulting compound represented by the formula (I),

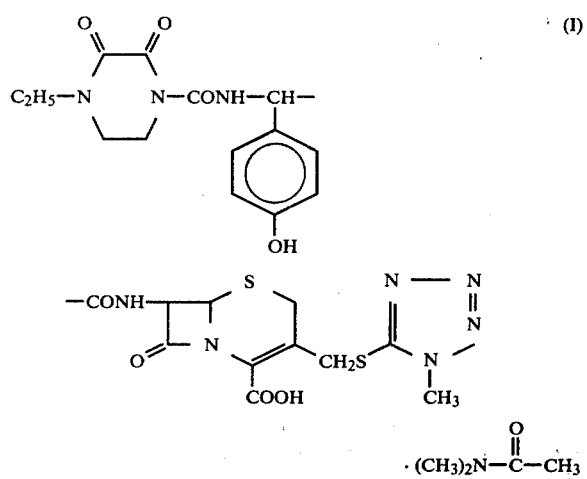

and treating said compound (I) with a solvent for N,N-dimethylacetamide to remove the N,N-dimethylacetamide and to liberate compound (II).

4. A process according to claim 1 or 3, wherein the reactive derivative of the compound represented by the formula (IV) is the acid halide of the compound represented by the formula (IV) or the reaction product of the compound represented by the formula (IV) with a Vilsmeier reagent.

5. A process according to claim 1 or 3, wherein the reactive derivative of the compound represented by the formula (IV) is the reaction product of the compound represented by the formula (IV) with a Vilsmeier reagent.

6. A process according to claim 1 or 3, wherein the acylation reaction is carried out at a temperature of −40° C. to 30° C.

7. A process according to claim 3, wherein the resulting compound represented by the formula (I) is treated with a solvent for N,N-dimethylacetamide selected from the group consisting of water, hydrophilic organic solvents, hydrophobic organic solvents, and mixtures of water and hydrophilic or hydrophobic organic solvents to remove the N,N-dimethylacetamide.

8. A process according to claim 7, wherein the solvent is selected from the group consisting of water and mixtures of water and hydrophilic organic solvents.

9. A process for producing purified 7-[D(−)-α-(4-ethyl-2,3-dioxo-1-piperazinecarboxamido)-α-(4-hydroxyphenyl)-acetamido]-3-[5-(1-methyl-1,2,3,4-tetrazolyl)-thiomethyl]Δ³-cephem-4-carboxylic acid represented by the formula (II),

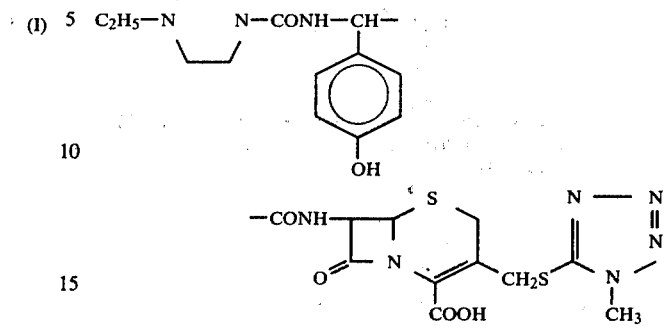

which comprises dissolving in dimethylacetamide the compound represented by the formula (II) associated with the by-products of its prior syntheses and thereafter precipitating from said solution the N,N-dimethylacetamide adduct of 7-[D(−)-α-(4-ethyl-2,3-dioxo-1-piperazinecarboxamido)-α-(4-hydroxyphenyl)acetamido]-3-[5-(1-methyl-1,2,3,4-tetrazolyl)thiomethyl]-Δ³-cephem-4-carboxylic acid represented by the formula (I),

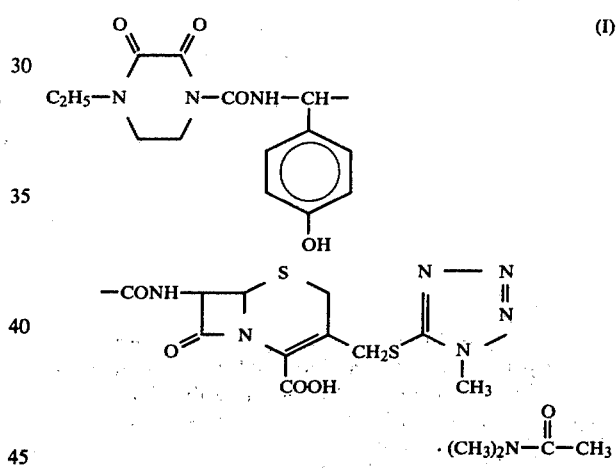

and then treating the N,N-dimethylacetamide adduct of the formula (I) with a solvent for N,N-dimethylacetamide to remove the N,N-dimethylacetamide and to liberate purified compound (II).

10. A process according to claim 8 wherein the compound (I) is stirred with aqueous methanol as the solvent.

11. A process according to claim 8 wherein the compound (I) is dissolved in aqueous acetonitrile in the presence of sodium hydrogen carbonate to form a solution and therefore hydrochloric acid is added to precipitate compound (II) from the solution.

12. A process according to claim 4 wherein in order to recover the resulting compound (I) as a precipitate water and a base to establish a pH of 1 to 3 are added to the solution of the acylated product.

* * * * *